United States Patent [19]

Lal

[11] Patent Number: 5,442,084
[45] Date of Patent: Aug. 15, 1995

[54] METHOD OF SELECTIVE FLUORINATION

[75] Inventor: Gauri S. Lal, Whitehall, Pa.

[73] Assignee: Air Products and Chemicals, Inc., Allentown, Pa.

[21] Appl. No.: 330,635

[22] Filed: Oct. 28, 1994

Related U.S. Application Data

[63] Continuation-in-part of Ser. No. 187,422, Jan. 25, 1994, abandoned.

[51] Int. Cl.$^6$ .......................... C07F 9/40; C07F 9/50; C07F 9/53
[52] U.S. Cl. ..................... 558/141; 558/385; 558/386; 560/227; 562/603; 568/16
[58] Field of Search ............................ 558/141; 568/16

[56] References Cited

U.S. PATENT DOCUMENTS

| | | | |
|---|---|---|---|
| 4,828,764 | 5/1989 | DesMarteau | 260/397.45 |
| 4,935,519 | 6/1990 | Van Der Puy et al. | 546/13 |
| 5,086,178 | 2/1992 | Banks | 544/351 |

OTHER PUBLICATIONS

Orchin, M. et al. *The Vocabulary of Organic Chemistry*. 1980; 375 and 415.

Herkes, F. E. and Burton, D. J. "Fluoro Olefins. I. The Synthesis of β-Substituted Perfluoro-Olefins." *J. Org. Chem.* 1967 (32): 1311–1318.

Burton, D. J. and Cox, D. G. "Wittig Olefination via Reaction of Fluorine-Containing Phosphoranium Sales and F-Acyl Fluorides. A New Approach to Fluoroolefin Synthesis". *J. Am. Chem. Soc.* 1983 (105):650–51.

Fuqua, S. A. et al. "Synthesis of 1,1-Difluoro Olefins. II. Reactions of Ketones with Tributylphosphine and Sodium Chlorodifluoroacetate." *J. Org. Chem.* Aug. 1965 (30):2543–45.

Suda, M. "Preparation and Reactivity of an α-(Difluoromethylene)-γ-Lactone." *Tetrahedron Letters* 1981 (22) No. 15: 1421–24.

Baader, E. et al. "Enantioselective Synthesis of a New Fluoro-Substituted HMG-COA Reductase Inhibitor." *Tetrahedron Letters* 1989 (30) No. 38: 5115–18.

McCarthy, J. R. et al. "A New Route to Vinyl Fluorides." *Tetrahedron Letters* 1990 (31) No. 38: 5449–52.

Obayashi, M. and Kondo, K. "Improved Procedure for the Synthesis of 1,1-Difluoro-2-Hydroxyalkylphosphonates." *Tetrahedron Letters* 1982 (23) No. 22: 2327–28.

Obayshi, M. et al. "(Diethylphosphinyl)difluoromethyllithium. Preparation and Synthetic Application." *Tetrahedron Letters* 1982 (23) No. 22: 2323–26.

Lal, G. S. "Site-Selective Fluorination of Organic Compounds Using 1-Alkyl-4-fluoro-1,4 diazabicyclo[2.2.2]octane Salts (Selectfluor Reagents)". *J. Org. Chem.* 1993 (58):2791–96.

Burton, D. J. and Herkes, F. E. "A One-Step Synthesis of B-Phenyl Substituted Perfluoroelfins." *Tetrahedron Letters* 1965 (23):1883–87.

Fried, J. et al. *Am. Chem Soc.* 1954, p. 1455.

Primary Examiner—Robert W. Ramsuer
Assistant Examiner—Michael G. Ambrose
Attorney, Agent, or Firm—Geoffrey L. Chase; William F. Marsh

[57] ABSTRACT

The present invention is a method for selectively fluorinating various methylenephosphonate and methylenephosphorane derivatives using an electrophilic fluorinating agent, such as N-fluoro 1,4-diazabicyclo[2.2.2] octane by fluorinating the monohalogenated methylenephosphonate or methylenephosphorane derivative to produce fluoromethylenephosphonate or fluoromethylenephosphorane derivatives useful as fluorinated Horner-Emmons or Wittig reagents in producing selectively fluorinated vinylic compounds.

20 Claims, No Drawings

METHOD OF SELECTIVE FLUORINATION

The present application is a continuation in part of U.S. application Ser. No. 08/187,422 filed Jan. 25, 1994, now abandoned.

FIELD OF THE INVENTION

An efficient synthesis of various fluoromethylenephosphonates and fluorinated methylenephosphoranes using non-fluorine halogenation and an electrophilic fluorinating reagent, such as 1-alkyl-4-fluoro-1,4-diazabicyclo[2.2.2]octane salts from methylenephosphonates and methylenephosphoranes is set forth.

BACKGROUND OF THE INVENTION

Since the discovery by Fried (Fried, J.; Subo, E. F., J. Am. Chem. Soc. 1954, p. 1455) of the increased therapeutic effect conferred by fluorine in 9α-fluorohydrocortisone acetate, a growing interest has emerged in the medicinal chemistry of organofluorine compounds. During the past 40 years, several useful advances in organofluorine chemistry have been translated into products of medicinal importance. The reason for this enhanced therapeutic activity has been rationalized mainly on the basis of the physicochemical properties of the fluorine atom in these compounds.

Wittig and Horner-Emmons reagents have served as versatile reagents for the generation of olefins from carbonyl groups, as described by M. Orchin, et al, in The Vocabulary of Organic Chemistry, 1980, pp. 415 and 375, respectively. The fluorinated versions of these compounds have also become very important owing to the interesting properties conferred by the vinylic fluorine atom in certain biologically active molecules. It has been found that incorporation of the fluoro-olefin functionality into substrates produces potent amine-oxidase inhibitors. This functional group has also been found useful as isoteric replacement for the amide group in peptides.

Several methods for the synthesis of the fluorinated Wittig and Horner-Emmons reagents have been reported. These compounds are generally obtained by the reaction of triphenylphosphine with halofluoromethane, as reported by Fuqua, S. A.; Duncan, W. G.; Silverstern, R. M. J. Org. Chem. 1965, 30, 2543: Burton, D. J.; Herkes, F. E. Tett. Lett. 1965, 1883 and Herkes, F. E.; Burton, D. J. J. Org. Chem. 1967, 32, 1311. This reaction in the presence of zinc to generate the zinc ylide has also been described, see Suda, M., Tetrahedron Letters, 1981, 22, No.15, pp 1421-1424. With trihalofluoromethane, it is possible to obtain a diphosphonium salt, see Burton, D. J.; Cox, D. G. J. Am. Chem. Soc. 1983, 105, 650. These reagents have been used to prepare fluoro-olefins via their reaction with aldehydes and ketones. However, the low yield of product, moisture sensitivity of reagents, high cost of starting materials and lack of reproducibility in reactions have limited the utility of these compounds.

The Horner-Emmons variation of the fluoro-Wittig reagents has also been used successfully to prepare fluoro-olefins, see Baader, E.; Bartmann, W.; Beck, Below, P.; Bergmann, A.; Jendralla, H.; Kesselar, K.; Wess, G.; Tetrahedron Letters, 1989, 30, 5115. These compounds can be obtained in a similar manner to their Wittig counterparts using difluorocarbons as starting material, see Obayashi, M.; Ito, E.; Mutsui, K.; Kondo, M. Tetrahedron Letters, 1982, 23, 2323; and Obayashi, M.; Kondo, M. Tetrahedron Letters, 1982, 23, 2327. Other methods include the reaction of diethylchlorophosphate with substituted fluoromethyl anions, per McCarthy, J. R.; Matthews, D. P.; Edwards, M. L.; Stemerick, D. M.; Jarvi, E. T.; Tetrahedron Letters, 1990, 31, 5449, and the reaction of phosphonate ylides with electrophilic fluorinating reagents, see Lal, G. S. J. Org. Chem. 1993, 58, 2791. These methods require expensive starting material, low temperature (−78° C.) in preparation or afford only low-to-moderate yields of products.

Electrophilic fluorination represents one of the most direct methods available for a selective introduction of fluorine into organic compounds. One of the earliest reagents employed for this purpose is perchlorylfluoride. Its application has declined dramatically owing to difficulties in handling and danger associated with its use. There are also fluorinating reagents incorporating the O-F bond including $CF_3OF$, $CF_3COOF$, and $CsSO_4F^6$. Although these are potent sources of electrophilic fluorine, the high reactivity of the compounds has contributed to low selectivity and the requirement for low-temperature conditions in many instances. Xenon difluoride has also been proven very effective for the fluorination of nucleophilic substrates, but its commercial use has been limited owing to its high cost of production. A new generation of electrophilic fluorinating reagents has emerged: molecules which incorporate a reactive N-F bond. These reagents, which are generally less reactive that those previously described, have proven to be relatively stable and selective for the fluorination of carbanionic organic substrates, see U.S. Pat. Nos. 4,828,764 and 4,935,519.

The synthesis and reactions of a very useful electrophilic fluorination reagent, 1-chloromethyl-4-fluoro-1,4-diazabicyclo(2.2.2)octane bis(tetrafluoroborate), have been reported in U.S. Pat. No. 5,086,178. This reagent is available from Air Products and Chemicals, Inc. as Selectfluor TM Reagent. This compound which is stable and easy to handle has been shown to effectively fluorinate various compounds.

The preparation of fluoromethylenephosphonate and fluoromethylenephosphorane derivatives and other Horner-Emmons and Wittig reagents by traditional fluorination and the reaction of previously fluorinated precursors have failed to produce such reagents in sufficient yields to be economically attractive and have required toxic and dangerous fluorination agents. The present invention overcomes these drawbacks as set forth below.

BRIEF SUMMARY OF THE INVENTION

The present invention is a method of synthesizing a product of the formula:

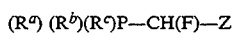

$(R^a)(R^b)(R^c)P\text{—}CH(F)\text{—}Z$ wherein $R^a$ is alkyl, aryl, alkyl substituted aryl, aryl substituted alkyl or hydrogen, each bonded directly or through an ether linkage to the phosphorus, or =O; $R^b$ is alkyl, aryl, alkyl substituted aryl, aryl substituted alkyl or hydrogen, each bonded directly or through an ether linkage to the phosphorus; $R^c$ is alkyl, aryl, alkyl substituted aryl, aryl substituted alkyl or hydrogen, each bonded directly or through an ether linkage to the phosphorus; and Z is —CN, —NO$_2$, —COR, —CO$_2$R, —PR$_3$, —P(O)OR$_2$, or organic compounds, (i.e., radicals) where R is alkyl, aryl, alkyl substituted aryl, aryl substituted alkyl or hydrogen; comprising selectively fluorinating with an electrophilic fluorinating agent a compound of the formula:

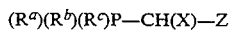

wherein $R^a$, $R^b$, $R^c$ and Z are as defined above and X is selected from the group consisting of I, Br and Cl, and reducing the resulting fluorinated compound to said product.

Preferably, the electrophilic fluorinating agent is selected from the group consisting of fluorine, xenon difluoride, perchloryl fluoride, trifluoromethyl hypofluorite, acetyl hypofluorite, trifluoroacetyl hypofluorite, phenyliododifluoride, perfluoro-N-fluoropiperidine, 1-fluoro-2-pyridone, N-fluoro-N-alkylsulfonamides, N-fluoroquinuclidinium fluoride, N-fluoropyridinium salts, N-fluoropyridinium pyridine heptafluorodiborate, N-fluoro-N-perfluoromethyl sulfonamide compounds, N-fluorobis[(trifluoromethyl)sulfonyl]imide, N-fluoro-N-arylsulfonimide, and 1-alkyl-4-fluoro-1,4-diazabicyclo[2.2.2]octane salt.

More preferably, the electrophilic fluorinating agent is a 1-alkyl-4-fluoro-1,4-diazabicyclo[2.2.2]octane salt. Most preferably, the electrophilic fluorinating agent is a 1-chloromethyl-4-fluoro-1,4-diazabicyclo[2.2.2]octane salt. Optimally, the electrophilic fluorinating agent is 1-chloromethyl-4-fluoro-1,4-diazabicyclo[2.2.2]octane bis (tetrafluoroborate).

Preferably, the compound is a halomethylenephosphonate derivative having the formula:

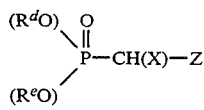

wherein $R^d$ and $R^e$ are hydrogen, alkyl, aryl, alkyl substituted aryl, aryl substituted alkyl and mixtures thereof; X is selected from the group consisting of I, Br and Cl; and Z is —CN, —NO$_2$, —COR, —CO$_2$R, —PR$_3$, —P(O)OR$_2$, or organic compounds, where R is alkyl, aryl, alkyl substituted aryl and aryl substituted alkyl or hydrogen.

Preferably, the product is a fluoromethylenephosphonate derivative having the formula:

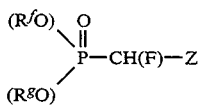

wherein $R^f$ and $R^g$ are hydrogen, alkyl, aryl, alkyl substituted aryl, aryl substituted alkyl and mixtures thereof; and Z is —CN, —NO$_2$, —COR, —CO$_2$R, —PR$_3$, —P(O)OR$_2$, or organic compounds, where R is alkyl, aryl, alkyl substituted aryl, aryl substituted alkyl or hydrogen.

More preferably, the fluoromethylenephosphonate is diethyl(phenylsulfonyl)fluoromethylenephosphonate.

Alternatively, the compound is a halo-methylenephosphorane derivative having the formula:

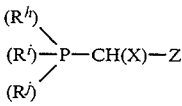

wherein $R^h$, $R^i$ and $R^j$ are hydrogen, alkyl, aryl, alkyl substituted aryl, aryl substituted alkyl and mixtures thereof; X is selected from the group consisting of I, Br and Cl; and Z is —CN, —NO$_2$, —COR, —CO$_2$R, —PR$_3$, —P(O)OR$_2$, or organic compounds, where R is alkyl, aryl, alkyl substituted aryl, aryl substituted alkyl or hydrogen.

Alternatively, the product is a fluoro-methylenephosphorane derivative having the formula:

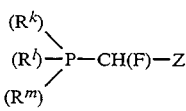

wherein $R^k$, $R^l$ and $R^m$ are hydrogen, alkyl, aryl, alkyl substituted aryl, aryl substituted alkyl and mixtures thereof; and Z is —CN, —NO$_2$, —COR, —CO$_2$R, —PR$_3$, —P(O)OR$_2$, or organic compounds, where R is alkyl, aryl, alkyl substituted aryl, aryl substituted alkyl or hydrogen.

Preferably, the fluorination is conducted in a solvent selected from the group consisting of tetrahydrofuran, dimethylformamide, hexane, acetonitrile, diethyl ether, nitromethane and mixtures thereof.

Preferably, a compound of the formula:

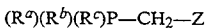

wherein $R^a$, $R^b$, $R^c$ and Z are as defined above, is halogenated in the methylene position with a halogen selected from the group consisting of I, Br and Cl, to produce the compound which is then fluorinated to produce the product.

The present invention is also a method for synthesizing fluoromethylenephosphonate derivatives by the selective iodization of a methylenephosphonate derivative at the methylene position to form an iodomethylenephosphonate derivative and then replacing the iodine by fluorination of said iodomethylenephosphonate derivative with an electrophilic fluorinating agent in an appropriate reaction media to produce the corresponding fluoromethylenephosphonate derivative.

The present invention is also a method for synthesizing fluoro-methylenephosphorane derivatives by the selective iodization of a methylenephosphorane derivative at the methylene position to form an iodo-methylenephosphorane derivative and then replacing the iodine by fluorination of said iodo-methylenephosphorane derivative with an electrophilic fluorinating agent in an appropriate reaction media to produce the corresponding fluoro-methylenephosphorane derivative.

DETAILED DESCRIPTION OF THE INVENTION

The present invention is directed to improvements in the selective fluorination of various methylenephosphonate and methylenephosphorane derivatives wherein one or more hydrogens of the methylene group are replaced with fluorine. Specifically, it is desirous to replace a single hydrogen with a fluorine. The selective fluorination of the present invention is particularly useful in the monofluorination of Horner-Emmons reagents and Wittig reagents, which can then be used to produce a corresponding monofluorinated vinylic compound. These fluorinated vinylic compounds find wide application in bio-active chemicals, such as pharmacological fluorine analogs to biologically active naturally occurring chemicals and synthetic drugs.

The Horner-Emmons reaction involves the conversion of a carbonyl group of an aldehyde or ketone to an olefinic group, wherein the carbanion of the Horner-Emmons reagent, such as a methylenephosphonate, attacks the carbonyl group resulting in the olefinic product having the carbon group of the aldehyde or ketone and the methylene group and any substituent of the Horner-Emmons reagent joined by the created double bond. Similar reactions occur in the Witting reaction when a Wittig reagent or methylenephosphorane is used to react with the carbonyl group of an aldehyde or ketone.

The electrophilic fluorination agent used in the present invention is any of the known electrophilic fluorinating agents, such as those that have a fluorine in a C-F bond in the fluorinating agent or a fluorine in a N-F bond in the fluorinating agent. Examples of such electrophilic fluorinating agents are fluorine, xenon difluoride, perchloryl fluoride, trifluoromethyl hypofluorite, acetyl hypofluorite, trifluoroacetyl hypofluorite, phenyliododifluoride, perfluoro-N-fluoropiperidine, 1-fluoro-2-pyridone, N-fluoro-N-alkylsulfonamides, N-fluoroquinuclidinium fluoride, N-fluoropyridinium salts, N-fluoropyridinium pyridine heptafluorodiborate, N-fluoro-N-perfluoromethyl sulfonamide compounds, N-fluorobis [(trifluoromethyl) sulfonyl]imide, N-fluoro-N-arylsulfonimide, and 1-alkyl-4-fluoro-1,4-diazabicyclo[2.2.2]octane salt. The latter agent is a compound N-fluorinated diazabicycloalkane of the formula:

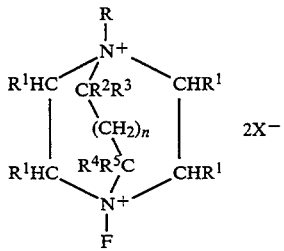

(I)

wherein n represents 0, 1 or 2; R represents a quaternizing organic group; each $R^1$, $R^2$, $R^3$, $R^4$ and $R^5$ independently represents hydrogen, $C_1$–$C_6$ alkyl, aryl, $C_1$–$C_6$ alkyl-substituted aryl or aryl-substituted $C_1$–$C_6$ alkyl; and each $X^-$ independently represents a counterion or $2X^-$ represents a single divalent counterion.

The group R can be any group which will quaternize one nitrogen atom of a diazabicycloalkane and is inert to the subsequent fluorination of the other nitrogen atom thereof in the sense that it does not prevent said fluorination. Suitable quaternizing groups include alkyl, optionally substituted by aryl and/or electron-withdrawing groups.

Alkyl groups represented by R can have 1 to 16, usually 1 to 8, especially 1 to 4, carbon atoms. Said alkyl groups can be substituted by aryl (including aromatic heterocyclic groups), especially phenyl and, additionally or alternatively, by one or more electron-withdrawing groups, especially halogen, particularly fluorine, or 1-azonia-azabicycloalkane, optionally quaternized at the second nitrogen atom by, for example, fluorine, particularly 4-fluoro-1,4-diazoniabicyclo[2.2.2]-octane (ie.

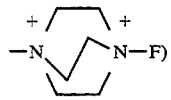

Presently, the preferred groups represented by R are:
(a) aliphatic unsubstituted linear or branched $C_1$–$C_{16}$ alkyl, especially $C_1$–$C_4$ alkyl, particularly methyl or ethyl;
(b) benzyl optionally substituted by up to three $C_1$–$C_4$ alkyl groups;
(c) $C_1$–$C_{10}$ perfluoroalkyl, for example trifluoro-methyl and perfluoro-octyl;
(d) $C_1$–$C_{16}$ partially halogenated alkyl, for example 2,2,2-trifluoroethyl or chloromethyl; and
(e) 3-(4-fluoro-1,4-diazoniabicyclo[2.2.2]oct-1-yl)- propyl (ie.

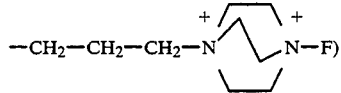

When any of $R^1$ to $R^5$ is other than hydrogen, it is preferably benzyl, phenyl or, especially, $C_1$–$C_4$ alkyl, particularly methyl. It will be understood that due to steric considerations it is not possible to obtain compounds of Formula I with all possible combinations of $R^1$ to $R^5$ values.

Usually no more than one $R^1$ at the 2 and 3 ring positions and no more than one $R^1$ at the 5 and 6 ring positions will be other than hydrogen. It is presently preferred that all $R^1$ are hydrogen.

Usually no more than one of $R^2$, $R^3$, $R^4$ and $R^5$ is other than hydrogen Presently it is preferred that all of $R^2$ to $R^5$ are hydrogen.

The counterion(s) represented by $2X^-$ can be any anion(s) which can be counterion(s) to the quaternizing group R. Usually, but not necessarily, the counterions will be weakly-nucleophilic. Suitable anions include halides, especially fluoride ($F^-$); fluorosulfate ($SO_3F^-$); alkanesulfonates, especially methanesulfonate ($CH_3SO_3^-$); alkyl sulfates, especially methyl sulphate ($CH_3SO_4^-$); perfluoroalkanesulfonates, preferably triflate ($CF_3SO_3^-$) and nonaflate ($C_4F_9SO_3^-$); arenesulfonates, especially tosylate (ie. p-toluenesulfonate; $CH_3C_6H_4SO_3^-$); alkanecarboxylates; perfluoroalkanecarboxylates; tetrafluoroborate ($BF_4^-$); tetraphenylborate ($Ph_4B^-$); hexafluorophosphate ($PF_6^-$); hexafluoroantimonate ($SbF_6^-$); chlorate ($ClO_3^-$); and sulfate ($SO_4^{--}=2X^-$). Presently preferred anions are fluoride, tetrafluoroborate, triflate and tosylate and it is presently particularly preferred that one $X^-$ is tosylate or triflate and the other $X^-$ is triflate.

It is preferred that n is 0, and each $R_1$ is hydrogen. Thus, according to a preferred embodiment, the invention uses N-fluorinated 1,4-diazabicyclo-[2.2.2[octane derivatives of the following Formula II

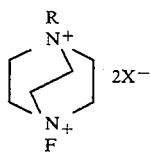

(II)

wherein R and X⁻ are as defined above. This class of electrophilic fluorinating agents are available from Air Products and Chemicals, Inc. as Selectfluor ™ agents.

The methylenephosphonate derivative which is fluorinated as the Horner-Emmons reagent is typically of the following formula:

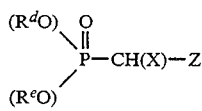

wherein $R^d$ and $R^e$ are hydrogen, alkyl, aryl, alkyl substituted aryl, aryl substituted alkyl or mixtures thereof; X is chlorine, bromine, iodine or hydrogen; and Z is —CN, —NO$_2$, —COR, —CO$_2$R, —PR$_3$, —P(O)OR$_2$, or organic compounds, (i.e., radical) where R is alkyl, aryl, alkyl substituted aryl, aryl substituted alkyl or hydrogen. The organic compounds for purposes of the present invention include various aliphatic, alicyclic, aromatic, and arene compounds that may or may not contain heteroatom substitution or functional groups containing oxygen, nitrogen or sulfur. Exemplary compounds are arylsulfonyls, such as phenylsulfonyl; alkylsulfonyl, such as methylsulfonyl; and alicyclic sulfonyl, such as cyclohexylsulfonyl. Other examples are; arylsulfoxides, such as phenylsulfoxide; alkylsulfoxide, such as methylsulfoxide; alicyclic sulfoxide, such as cyclohexylsulfoxide; arylsulfides, such as thiophenyl; alkylsulfide, such as thiomethyl; and alicyclic sulfides, such as thiocyclohexyl. Additional examples include; aryloxides, such as phenoxide; alkyloxides, such as methoxide; alicyclic oxides, such as cyclohexyloxide; arylamines, such as phenylamine; alkylamines, such as methylamine and alicyclic amines, such as cyclohexylamine. Preferably, the methylenephosphonate derivative is diethyl (phenyl sulfonyl)methylenephosphonate.

The methylenephosphorane derivative which is fluorinated as the Wittig reagent is typically a halomethylenephosphorane derivative having the formula:

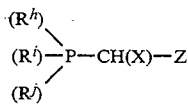

wherein $R^h$, $R^i$ and $R^j$ are hydrogen, alkyl, aryl, alkyl substituted aryl, aryl substituted alkyl and mixtures thereof; X is selected from the group consisting of I, Br and Cl; and Z is —CN, —NO$_2$, —COR, —CO$_2$R, —PR$_3$, —P(O)OR$_2$, or organic compounds, where R is alkyl, aryl, alkyl substituted aryl, aryl substituted alkyl or hydrogen. Again, the organic compounds for purposes of the present invention include various aliphatic, alicyclic, aromatic, and arene compounds that may or may not contain heteroatom substitution or functional groups containing oxygen, nitrogen or sulfur. Exemplary compounds are arylsulfonyls, such as phenylsulfonyl; alkylsulfonyl, such as methylsulfonyl; and alicyclic sulfonyl, such as cyclohexylsulfonyl. Other examples are; arylsulfoxides, such as phenylsulfoxide; alkylsulfoxide, such as methylsulfoxide; alicyclic sulfoxide, such as cyclohexylsulfoxide; arylsulfides, such as thiophenyl; alkylsulfide, such as thiomethyl; and alicyclic sulfides, such as thiocyclohexyl. Additional examples include; aryloxides, such as phenoxide; alkyloxides, such as methoxide; alicyclic oxides, such as cyclohexyloxide; arylamines, such as phenylamine; alkylamines, such as methylamine and alicyclic amines, such as cyclohexylamine.

Preferably, the fluorination is conducted in a solvent selected from the group consisting of tetrahydrofuran, dimethylformamide, hexane, acetonitrile, diethyl ether, nitromethane and mixtures thereof.

If the solvent does not provide sufficient reducing capability to remove the halogen from the fluoro,halo-intermediate then a reducing agent is added to the solvent, such as; sodium hydride, sodium bisulfate, sodium dithionite, zinc and various hydrides. Typically, the fluoro,iodo-intermediate will reduce to the fluorinated product without additional reducing agent.

In an exemplary embodiment the present invention is carried out by selecting an appropriate N-fluoro derivative of 1,4-diazabicyclo[2.2.2]octane which is reacted with the anion generated from diethyl(phenylsulfonyl)-methylenephosphonate and NaH at room temperature to produce a mixture of diethyl(phenylsulfonyl) fluoromethylenephosphonate (60%) and diethyl (phenylsulfonyl)difluoromethylenephosphonate (15%) with starting material (25%) remaining on completion of the reaction.

This fluorination was studied under a variety of reaction conditions including solvents, temperatures, bases and order of addition of phosphonate to fluorination reagent. Using tetrahydrofuran and methylcyanide (THF/CH$_3$CN) or tetrahydrofuran and dimethylformamide (THF/DMF), no discernible change in the ratio of mono to difluorinated products were observed. At 0° C., there was a small increase in the formation of the difluorinated product compared to room temperature, but no change in product distribution was observed at higher temperatures (up to 66°). Variation of the metal counter ion (Li$^+$, Na$^+$, K$^+$) as a result of generating the methylenephosphorane using n-butyl lithium, sodium hydride or potassium tert-butoxide, followed by fluorination did not produce any dramatic change (<54) in the ratio of mono to difluorinated products. The order of addition of substrate to reagent also showed no significant change in the products obtained. These results indicate that the carbanion generated from diethyl(phenylsulfonyl)methylenephosphonate rapidly deprotonates the monofluorinated product to form a fluorophosphonate ylide which is then fluorinated by the subject fluorinating reagent.

A similar sequence of reactions, but utilizing N-bromosuccinimide (NBS) to generate the corresponding diethyl(phenylsulfonyl) bromomethylenephosphonate intermediate gave the diethyl (phenylsulfonyl) bromofluoromethylenephosphonate after fluorination. This compound was rapidly debrominated with NaHSO$_3$ to afford the monofluorinated product, diethyl (phenylsulfonyl)fluoromethylenephosphonate, in 75% overall yield. In this case, some diethyl (phenylsulfonyl)dibromomethylenephosphonate. (12%) was obtained, and there was some hydrolysis of the intermediate bromofluoromethylenephosphonate which afforded bromofluoromethylenephenyl sulfone (9%) after reduction with NaHSO$_3$. The chloromethylenephosphonate analog proved to be less useful. Fluorination of the sodium salt of diethyl(phenylsulfonyl)chloromethylenephosphonate produced a 2.1 mixture of diethyl(phenylsulfonyl) chlorofluoromethylenephosphonate chlorofluoromethylenephenylsulfone. The latter presumably resulted from hydrolysis of the diethyl(phenylsulfonyl)-chlorofluoromethylenephosphonate.

A high yield, virtually one pot process has been developed for the synthesis of diethyl(phenylsulfonyl)-fluoromethylenephosphonate. This method utilizes commercially available electrophilic fluorination reagent, such as the Selectfluor Reagent, and offers a simple access to the fluorinated Horner-Emmons reagent.

The experimental protocol for the following experiments and the source of the various reactants were as follows. The phosphonate starting material, diethyl(phenylsulfonyl)methylenephosphonate was obtained via a standard literature procedure by oxidation of diethylphenylthiomethylenephosphonate. The reagents, sodium hydride, n-butyl lithium, potassium tert-butoxide, N-iodosuccinimide (NIS), N-bromosuccinimide (NBS), N-chlorosuccinimide (NCS), sodium bisulfite were obtained from Aldrich Chemical and used as such. The Selectfluor TM Reagent was obtained from IGD, Specialty Gas, Air Products and Chemicals, Inc. The solvents, $CH_3CN$ and DMF were dried with calcium hydride prior to use. THF was dried with sodium/benzophenone before use NMR spectra were obtained on a Brucker ACP-300 FT spectrometer operating at 282.4 MHz ($^{19}F$), 300.13 MHz ($^1H$). Chemical shifts were referenced to neat $CFCl_3$ ($^{19}F$) or $CHCl_3$ ($^1H$)

EXPERIMENT 1

Synthesis of diethyl(phenylsulfonyl)fluoromethylenephosphonate from diethyl(phenylsulfonyl)methylenephosphonate directly A solution of diethyl(phenylsulfonyl)methylenephosphonate (584 mg, 2 mmol) in THF (5.0 mL) under $N_2$ was added to a suspension of oil-free NaH (48 mg, 80 mg of 60%, 2 mmol) at 0° C. and stirred until $H_2$ evolution ceased. The solution was then diluted with DMF (5.0 mL), brought to room temperature, Selectfluor TM Reagent (1) (707 mg, 787 mg of 90%) was added and the solution was stirred at room temperature for 30 minutes. The mixture was poured into ethylacetate, EtOAc, (50.0 mL), washed with $H_2O$ (2×25 mL), saturated $NaHCO_3$ (25 mL), dried ($MgSO_4$) and evaporated in vacuo. Flash chromatography on silica gel (7/3 ethylacetate/hexane) afforded diethyl (phenylsulfonyl)-fluoromethylenephosphonate (373 mg, 60%), $^1H$ NMR ($CDCl_3$) $\delta$7.9 (d, 2H), 7.65 (t, 1H), 7.55 (t, 2H), 5.35 (dd, 1H), 4.45–4.15 (m, 4H), 1.30 (t, 6H), $^{19}F$ NMR ($CDCl_3$) $\delta$-194.5 (dd, 1F); and diethyl (phenylsulfonyl)difluoromethylenephosphonate (99 mg, 15%), $^1H$ NMR $\delta$ 7.9 (d,2H), 7.60 (t,1H) 7.50 (t,2H), 4.2–4.0 (m, 4H) 1.25–1.15 (m, 6H) $^{19}F$ NMR ($CDCl_3$) $\delta$-108 (d, 2F). The diethyl(phenylsulfonyl)-difluoromethylenephosphonate was hydrolyzed to produce difluoromethylphenylsulfone. Difluoromethylphenylsulfone can be useful as a precursor to terminal difluoroolefins which can be obtained on reaction of the sulfone ylide with aldehydes and ketones, mesylation of the intermediate alcohol and reductive elimination of the sulfone entity.

EXPERIMENT 2

Synthesis of diethyl(phenylsulfonyl)fluoromethylenephosphonate from diethyl(phenylsulfonyl)methylenephosphonate via diethyl(phenylsulfonyl)iodomethylenephosphonate A solution of diethyl(phenylsulfonyl)methylenephosphonate (648 mg, 2.22 mmol) in THF (8.0 mL) under $N_2$ was added to a suspension of oil-free NaH (89 mg of 60%, 2.22 mmol) in THF (8.0 mL) at 0° C. The mixture was stirred at 0° C. until $H_2$ evolution ceased and then brought to room temperature. The solution was treated with NIS (500 mg, 2.22 mmol) and stirred for 10 minutes. This suspension was then added to an oil-free suspension of NaH (89 mg of 60%, 2.22 mmol) at 0° C. and stirred until $H_2$evolution ceased (~30 min.). The suspension was then diluted with DMF (8.0 ml) and the fluorinating reagent 1-chloromethyl-4-fluoro-1,4-diazabicyclo[2.2.2]octane bis(tetrafluoroborate) (873 mg of 90%, 780 mg, 2.22 mmol) was added. The mixture was stirred for 10 minutes, then brought to room temperature and stirred for 5 minutes. The mixture was poured into EtOAc (50 mL), washed with saturated aqueous $NaHSO_3$ (20 mL), dried ($MgSO_4$), filtered and evaporated in vacuo. Flash chromatography on silica gel (7:3 ethyl acetate/hexane) afforded the pure product, diethyl (phenylsulfonyl)fluoromethylenephosphonate, (579 mg, 84%).

EXPERIMENT 3

Synthesis of diethyl (phenylsulfonyl)fluoromethylenephosphonate from diethyl (phenylsulfonyl)methylenephosphonate via diethyl (phenyl(phenylsulfonyl)-bromodomethylenephosphonate Using NBS instead of NIS and following the procedure outlined above, diethyl(phenylsulfonyl)bromofluoromethylenephosphonate (735 mg, 85%) was obtained after fluorination and purification by flash chromatography on silica gel (1:1 ethylacetate/hexane), $^1H$ NMR ($CDCl_3$) $\delta$7.95 (d, 2H), 7.70 (t, 1H), 7.55 (t, 2H), 4.45–4.15 (m, 4H), 1.40–1.20 (m,6H), $^{19}F$ NMR ($CDCl_3$) $\delta$-125 (d, 1F). The diethyl (phenylsulfonyl)bromofluoromethylenephosphonate in EtOAc (50 mL) was stirred with 20 mL of saturated aqueous $NaHSO_3$ for 10 minutes. The aqueous phase was extracted into EtOAc. The organic extracts were dried ($MgSO_4$), filtered and evaporated in a vacuo to afford 523 mg (75%) of diethyl (phenylsulfonyl)fluoromethylenephosphonate and bromofluoromethylenephenylsulfone (52 mg, 9%), $^1H$ NMR ($CDCl_3$), $\delta$7.90 (d, 2H), 7.75 (t, 1H), 7.65 (t, 2H), 6.85 (d, 1H), $^{19}F$ NMR ($CDCl_3$) $\delta$-140 (d, 1F).

EXPERIMENT 4

Synthesis of diethyl(phenylsulfonyl)fluoromethylenephosphonate via diethyl (phenysulfonyl)iodomethylenephosphonate using 1-fluoro-2,4,6-trimethylpyridinium triflate A solution of diethyl(phenylsulfonyl)methylenephosphonate (584 mg, 2 mmol) in tetrahydrofuran (THF) (8.0 mL) under $N_2$ was added to a suspension of oil-free Nail (80 mg of 60%, 2.0 mmol) in THF at 0° C.

The mixture was stirred at 0° C. until $H_2$ evolution ceased and then brought to room temperature. The solution was treated with N-Iodosuccinimide (450 mg, 2 mmol) and stirred for 10 minutes. This suspension was added to an oil-free suspension of NaH (80 mg of 60%, 2.0 mmol) at 0° C. and stirred until $H_2$ evolution ceased (~30 minutes). The suspension was diluted with THF (8.0 mL) and the fluorinating reagent, 1-fluoro-2,4,6-trimethylpyridinium triflate (578 mg, 2 mmol) was added. The mixture was stirred for 30 minutes, then brought to room temperature and stirred for 30 minutes.

The mixture was poured into EtOAc (50 mL), washed with saturated aqueous NaHSO₃ (20 mL), dried (MgSO₄), filtered and evaporated in vacuo. Flash chromatography on silica gel afforded the pure product (341 mg, 55%).

EXPERIMENT 5

Synthesis of diethyl (phenylsulfonyl)fluoromethylenephosphonate via diethyl(phenylsulfonyl)iodomethylenephosphonate using N-fluorobenzenesulfonimide A solution of diethyl(phenylsulfonyl)methylenephosphonate (584 mg, 2 mmol) in tetrahydrofuran (THF) (8.0 mL) under N₂ was added to a suspension of oil-free NaH (80 mg of 60%, 2.0 mmol) in THF at 0° C. The mixture was stirred at 0° C. until H₂ evolution ceased and then brought to room temperature. The solution was treated with N-Iodosuccinimide (450 mg, 2 mmol) and stirred for 10 minutes. This suspension was added to an oil-free suspension of NaH (80 mg of 60%, 2.0 mmol) at 0° C. and stirred until H₂ evolution ceased (~30 minutes). The suspension was diluted with THF (8.0 mL) and the fluorinating reagent, N-fluorobenzenesulfonimide (632 mg, 2 mmol) was added. The mixture was stirred for 30 minutes, then brought to room temperature and stirred for 30 minutes. The mixture was poured into EtOAc (50 mL), washed with saturated aqueous NaHSO₃ (20 mL), dried (MgSO₄), filtered and evaporated in vacuo. Flash chromatography on silica gel afforded the pure product (329 mg, 53%).

EXPERIMENT 6

Synthesis of triphenyl(phenylsulfonyl)fluoromethylphosphorane via tripheryl(phenylsulfonyl)iodomethylenephosphorane A solution of triphenyl(phenylsulfonyl)methanephosphorane (834 mg, 2 mmol) in tetrahydrofuran (THF) (8.0 mL) under N₂ can be added to a suspension of oil-free NaH (80 mg of 60%, 2.0 mmol) in THF at 0° C. This mixture can be stirred at 0° C. until H₂ evolution ceases and then can be brought to room temperature. N-Iodosuccinimide (450 mg, 2 mmol) can be added to the solution and stirring can be continued for 10 minutes. This suspension can then be added to an oil-free suspension of NaH (80 mg of 604%, 2.0 mmol) at 0° C. in THF and can be stirred until H₂ evolution will have ceased (~30 minutes). The suspension will be diluted with dimethylformamide (DMF) (8.0 mL) and the fluorinating reagent 1-chloromethyl-4-fluoro-1,4-diazabicyclo[2.2.2]octane bis(tetrafluoroborate) (787 mg of 90%, 708 mg, 2.0 mmol) will be added. The mixture can be stirred for 10 minutes and then can be brought to room temperature. Stirring can be continued for 5 minutes. The mixture will be poured into EtOAc (50 mL) and can be washed with saturated aqueous NaHSO₃ (20 mL). The solvent can be dried (MgSO₄), filtered and evaporated. The residue can be chromatographed on silica gel (7:3 ethyl acetate/hexane) in order to obtain the pure product.

As can be clearly seen from the comparison of the above examples, the method of the present invention provides an unexpected and significant yield of the desired fluorinated product over the known methods and the high yield product will be useful and positively effect the economics of fluorovinylic chemicals and especially pharmaceuticals using the product of the present invention in the Horner-Emmons and Wittig syntheses.

The present invention has been set forth with regard to several preferred embodiments, but the full scope of the invention should be ascertained from the claims which follow.

I claim:

1. A method of synthesizing a product of the formula:

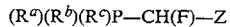

wherein $R^a$ is alkyl, aryl, alkyl substituted aryl, aryl substituted alkyl or hydrogen, each bonded directly or through an ether linkage to the phosphorus, or =O; $R^b$ is alkyl, aryl, alkyl substituted aryl, aryl substituted alkyl or hydrogen, each bonded directly or through an ether linkage to the phosphorus; $R^c$ is alkyl, aryl, alkyl substituted aryl, aryl substituted alkyl or hydrogen, each bonded directly or through an ether linkage to the phosphorus; and Z is —CN, —NO₂, —COR, —CO₂R, —PR₃, —P(O)OR₂, or an organic radical, where R is alkyl, aryl, alkyl substituted aryl, aryl substituted alkyl or hydrogen; comprising selectively fluorinating with an electrophilic fluorinating agent a compound of the formula:

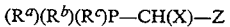

wherein $R^a$, $R^b$, $R^c$ and Z are as defined above and X is selected from the group consisting of I, Br and Cl, and reducing the resulting fluorinated compound to said product.

2. The method of claim 1 wherein said electrophilic fluorinating agent is selected from the group consisting of fluorine, xenon difluoride, perchloryl fluoride, trifluoromethyl hypofluorite, acetyl hypofluorite, trifluoroacetyl hypofluorite, phenyliododifluoride, perfluoro-N-fluoropiperidine, 1-fluoro-2-pyridone, N-fluoro-N-alkylsulfonamides, N-fluoroquinuclidinium fluoride, N-fluoropyridinium salts, N-fluoropyridinium pyridine heptafluorodiborate, N-fluoro-N-perfluoromethyl sulfonamide compounds, N-fluorobis[(trifluoromethyl)sulfonyl]imide, N-fluoro-N-arylsulfonimide, and 1-alkyl-4-fluoro-1,4-diazabicyclo[2.2.2]octane salt.

3. The method of claim 1 wherein said electrophilic fluorinating agent is a 1-alkyl-4-fluoro-1,4-diazabicyclo[2.2.2]octane salt.

4. The method of claim 1 wherein said electrophilic fluorinating agent is a 1-chloromethyl-4-fluoro-1,4-diazabicyclo[2.2.2[octane salt.

5. The method of claim 1 wherein said electrophilic fluorinating agent is 1-chloromethyl-4-fluoro-1,4-diazabicyclo[2.2.2]octane bis(tetrafluoroborate).

6. The method of claim 1 wherein said compound is a halomethylenephosphonate derivative having the formula:

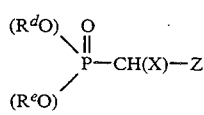

wherein $R^d$ and $R^e$ are hydrogen, alkyl, aryl, alkyl substituted aryl, aryl substituted alkyl and mixtures thereof; X is selected from the group consisting of I, Br and Cl; and Z is —CN, —NO₂, —COR, —CO₂R, —PR₃, —P(O)OR₂, or an organic radical, where R is alkyl, aryl, alkyl substituted aryl, aryl substituted alkyl or hydrogen.

7. The method of claim 1 wherein said product is a fluoromethylenephosphonate derivative having the formula:

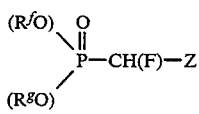

wherein $R^f$ and $R^g$ are hydrogen, alkyl, aryl, alkyl substituted aryl, aryl substituted alkyl and mixtures thereof; and Z is —CN, —NO$_2$, —COR, —CO$_2$R, —PR$_3$, —P(O)OR$_2$, or an organic radical, where R is alkyl, aryl, alkyl substituted aryl, aryl substituted alkyl or hydrogen.

8. The method of claim 7 wherein said fluoromethylenephosphonate is diethyl(phenylsulfonyl)-fluoromethylenephosphonate.

9. The method of claim 1 wherein said compound is a halomethylenephosphorane derivative having the formula:

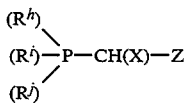

wherein $R^h$, $R^i$ and $R^j$ are hydrogen alkyl aryl alkyl substituted aryl, aryl substituted alkyl and mixtures thereof; X is selected from the group consisting of I, Br and Cl; and Z is —CN, —NO$_2$, —COR, —CO$_2$R, —PR$_3$, —P(O)OR$_2$, or an organic radical, where R is alkyl, aryl, alkyl substituted aryl, aryl substituted alkyl or hydrogen.

10. The method of claim 1 wherein said product is a fluoromethylenephosphorane derivative having the formula:

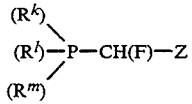

wherein $R^k$, $R^l$ and $R^m$ are hydrogen, alkyl, aryl, alkyl substituted aryl, aryl substituted alkyl and mixtures thereof; and Z is —CN, —NO$_2$, —COR, —CO$_2$R, —PR$_3$, —P(O)OR$_2$, or an organic radical, where R is alkyl, aryl, alkyl substituted aryl, aryl substituted alkyl or hydrogen.

11. The method of claim 1 wherein the fluorination is conducted in a solvent selected from the group consisting of tetrahydrofuran, dimethylformamide, hexane, acetonitrile, diethyl ether, nitromethane and mixtures thereof.

12. The method of claim 1 wherein a compound of the formula:

a compound of the formula $(R^1)$ $(R^b)$ $(R^c)$ P—CH(X)—Z is halogentated in the methylene position with a halogen selected from the group consisting of I, Br and Cl, to produce said compound which is then fluorinated to produce said product.

13. A method for synthesizing fluoromethylenephosphonate derivatives by the selective iodization of a methylenephosphonate derivative at the methylene position to form an iodomethylenephosphonate derivative and then replacing the iodine by fluorination of said iodomethylenephosphonate derivative with an electrophilic fluorinating agent in an appropriate reaction media to produce the corresponding fluoromethylenephosphonate derivative.

14. The method of claim 13 wherein said electrophilic fluorinating agent is a 1-alkyl-4-fluoro-1,4-diazabicyclo[2.2.2]octane salt.

15. The method of claim 13 wherein said electrophilic fluorinating agent is a 1-chloromethyl-4-fluoro-1,4-diazabicyclo[2.2.21]octane salt.

16. The method of claim 13 wherein said electrophilic fluorinating agent is 1-chloromethyl-4-fluoro-1,4-diazabicyclo[2.2.21]octane bis(tetrafluoroborate).

17. A method for synthesizing fluoro-methylenephosphorane derivatives by the selective iodization of a methylenephosphorane derivative at the methylene position to form an iodo-methylenephosphorane derivative and then replacing the iodine by fluorination of said iodo-methylenephosphorane derivative with an electrophilic fluorinating agent in an appropriate reaction media to produce the corresponding fluoromethylenephosphorane derivative.

18. The method of claim 17 wherein said electrophilic fluorinating agent is a 1-alkyl-4-fluoro-1,4-diazabicyclo[2.2.2]octane salt.

19. The method of claim 17 wherein said electrophilic fluorinating agent is a 1-chloromethyl-4-fluoro-1,4-diazabicyclo[2.2.2]octane salt.

20. The method of claim 17 wherein said electrophilic fluorinating agent is 1-chloromethyl-4-fluoro-1,4-diazabicyclo[2.2.2]octane bis(tetrafluoroborate).

* * * * *

UNITED STATES PATENT AND TRADEMARK OFFICE
CERTIFICATE OF CORRECTION

PATENT NO. : 5,442,084
DATED : Aug. 15, 1995
INVENTOR(S) : Gauri S. Lal

It is certified that error appears in the above-indentified patent and that said Letters Patent is hereby corrected as shown below:

Column 14, lines 10 and 11, delete "a compound of the formula $(R1)$ $(R^b)$ $(R^c)$ P--CH(X)--Z".

Column 14, line 13, delete "said compound" and replace with -- a compound of the formula $(R^a)$ $(R^b)$ $(R^c)$ P--CH (X)--Z --.

Signed and Sealed this

Seventeenth Day of October, 1995

Attest:

BRUCE LEHMAN

*Attesting Officer*       *Commissioner of Patents and Trademarks*